(12) United States Patent
Naylor et al.

(10) Patent No.: US 7,026,327 B2
(45) Date of Patent: Apr. 11, 2006

(54) PYRIMIDINE DERIVATIVES USEFUL AS SELECTIVE COX-2 INHIBITORS

(75) Inventors: Alan Naylor, Stevenage (GB); Jeremy John Payne, Stevenage (GB); Neil Anthony Pegg, Stevenage (GB)

(73) Assignee: Glaxo Group Limited (GB)

( * ) Notice: Subject to any disclaimer, the term of this patent is extended or adjusted under 35 U.S.C. 154(b) by 186 days.

(21) Appl. No.: 10/477,547

(22) PCT Filed: May 23, 2002

(86) PCT No.: PCT/GB02/02415

§ 371 (c)(1),
(2), (4) Date: Apr. 27, 2004

(87) PCT Pub. No.: WO02/096885

PCT Pub. Date: Dec. 5, 2002

(65) Prior Publication Data

US 2005/0032821 A1 Feb. 10, 2005

(30) Foreign Application Priority Data

May 25, 2001 (GB) ............................................. 0112802

(51) Int. Cl.
C07D 239/34 (2006.01)
C07D 401/12 (2006.01)
A61K 31/505 (2006.01)

(52) U.S. Cl. ........................ 514/269; 544/315; 544/318

(58) Field of Classification Search .................. 544/315, 544/318; 514/269
See application file for complete search history.

(56) References Cited

U.S. PATENT DOCUMENTS

| 3,149,109 A | 9/1964 | Neustaedter et al. ........ 260/251 |
| 3,592,895 A | 7/1971 | Hepworth et al. .......... 424/251 |
| 5,474,995 A | 12/1995 | Ducharme et al. .......... 514/241 |

(Continued)

FOREIGN PATENT DOCUMENTS

| DE | 19909541 | 3/1999 |
| JP | 9241161 | 9/1997 |
| WO | WO 9607641 | 3/1996 |

(Continued)

OTHER PUBLICATIONS

Simone, J.V., "Oncology: Introduction" Cecil Texbook of Medicine, 20th Edition, vol. 1, pp. 1004–1010, 1996.
Layzer, R.B., "Degenerative Diseases of the Nervous System" Cecil Textbook of Medicine, 20th Edition, vol. 2, pp. 2050–2057, 1996.

(Continued)

Primary Examiner—Deepak Rao
(74) Attorney, Agent, or Firm—Lorie Ann Morgan

(57) ABSTRACT

The invention provides the compounds of formula (I)

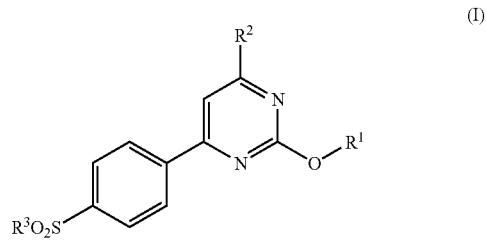

(I)

in which:
$R^1$ is selected from the group consisting of H, $C_{1-6}$alkyl, $C_{1-2}$alkyl substituted by one to five fluorine atoms, $C_{3-6}$alkenyl, $C_{3-6}$alkynyl, $C_{3-10}$cycloalkyl$C_{0-6}$alkyl, $C_{4-12}$bridged cycloalkyl, $A(CR^4R^5)_n$ and $B(CR^4R^5)_n$;
$R^2$ is $C_{1-2}$alkyl substituted by one to five fluorine atoms;
$R^3$ is selected from the group consisting of $C_{1-6}$alkyl, $NH_2$ and $R^7CONH$;
$R^4$ and $R^5$ are independently selected from H or $C_{1-6}$alkyl;
A is an unsubstituted 5- or 6-membered heteroaryl or an unsubstituted 6-membered aryl, or a 5- or 6-membered heteroaryl or a 6-membered aryl substituted by one or more $R^6$;
$R^6$ is selected from the group consisting of halogen, $C_{1-6}$alkyl, $C_{1-6}$alkyl substituted by one more fluorine atoms, $C_{1-6}$alkoxy, $C_{1-6}$alkoxy substituted by one or more F, $NH_2SO_2$ and $C_{1-6}$alkylSO$_2$;
B is selected from the group consisting of

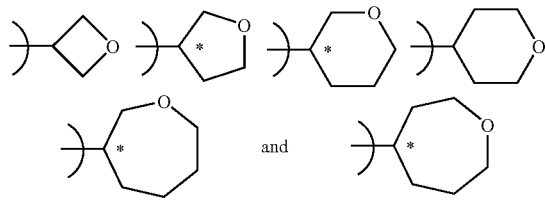

where

)

defines the point of attachment of the ring;
$R^7$ is selected from the group consisting of H, $C_{1-6}$alkyl, $C_{1-6}$alkoxy, $C_{1-6}$alkylOC$_{1-6}$alkyl, phenyl, HO$_2$CC$_{1-6}$alkyl, $C_{1-6}$alkylOCOC$_{1-6}$alkyl, $C_{1-6}$alkylOCO, H$_2$NC$_{1-6}$alkyl, $C_{1-6}$alkylOCONHC$_{1-6}$alkyl and $C_{1-6}$alkylCONHC$_{1-6}$alkyl; and
n is 0 to 4.
Compounds of formula (I) are potent and selective inhibitors of COX-2 and are of use in the treatment of the pain, fever and inflammation of variety of conditions and diseases.

37 Claims, No Drawings

U.S. PATENT DOCUMENTS

| | | | |
|---|---|---|---|
| 5,760,068 A | 6/1998 | Talley et al. | 514/403 |
| 5,972,986 A | 10/1999 | Seibert et al. | 514/210 |
| 6,020,343 A | 2/2000 | Gauther et al. | 514/232.5 |
| 6,153,619 A | 11/2000 | Wood et al. | 514/269 |
| 6,306,866 B1 | 10/2001 | Wood et al. | 514/274 |
| 6,313,072 B1 | 11/2001 | Scheiblich et al. | 504/242 |
| 6,780,869 B1 | 8/2004 | Green et al. | 514/275 |
| 6,780,870 B1 | 8/2004 | Carter et al. | 514/275 |
| 2003/0013717 A1 | 1/2003 | Mangel et al. | 514/248 |

FOREIGN PATENT DOCUMENTS

| | | |
|---|---|---|
| WO | WO 96 24585 | 8/1996 |
| WO | WO 96 41625 | 12/1996 |
| WO | WO 96 41645 | 12/1996 |
| WO | WO/98/03484 | 1/1998 |
| WO | WO 98 16227 | 4/1998 |
| WO | WO/98/24782 | 6/1998 |
| WO | WO 99 01439 | 1/1999 |
| WO | WO/01/38311 | 5/2001 |
| WO | WO/01/58881 | 8/2001 |
| WO | WO/02/18374 | 3/2002 |
| WO | WO/02/096427 | 12/2002 |
| WO | WO/02/096885 | 12/2002 |
| WO | WO/02/096886 | 12/2002 |

OTHER PUBLICATIONS

Damasio, A.R. "Alzheimer's Disease and Related Dementias" Cecil Textbook of Medicine, $20^{th}$ Edition, vol. 2, pp 1992–1996, 1996.

Freston, JW. "Rationalizing Cyclooxygenase (COX) Inhibition for Maximal Efficacy and Minimal Adverse Events & Discussion." PubMed Abstract, Am J Med 107(6A):78S–88S, Discussion 89S), Dec. 1999.

Naesdal, J. et al. "Gastro–Duodenal Protection in an Era of Cyclo–Oxygenase–2–Selective Nonsteroidal Anti–inflammatory Drugs." PubMed Abstract, Eur J Gastroenterol Hepatol, 13(12):1401–1406, Dec. 2001.

Douglas, R.G., Jr. Introduction to Viral Diseases: Cecil Textbook of Medicine, $20^{th}$ Edition, vol. 2, pp. 1739–1747, 1996.

PYRIMIDINE DERIVATIVES USEFUL AS SELECTIVE COX-2 INHIBITORS

CROSS REFERENCES TO RELATED APPLICATIONS

This application is a 371 Application of PCT/GB02/02415, filed 23 May 2002, which claims priority to GB Application Serial No. 0112802.4, filed 25 May 2001.

This invention related to pyrimidine derivatives, to processes for their preparation, to phamaceutical compositions containing them and to their use in medicine.

The enzyme cyclooxygenase (COX) has recently been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is largely responsible for the important physiological functions such as maintenance of gastrointestinal integrity and renal blood flow. In contrast the inducible form, COX-2, is believed to be largely responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyretic and analgesic properties, without the potential side effects associated with inhibition of COX-1. We have now found a novel group of compounds which are both potent and selective inhibitors of COX-2.

The invention thus provides the compounds of formula (I)

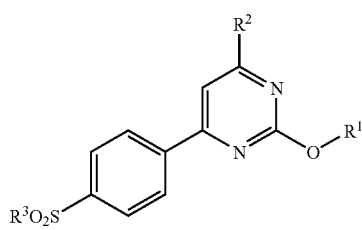

(I)

in which:
$R^1$ is selected from the group consisting of H, $C_{1-6}$alkyl, $C_{1-2}$alkyl substituted by one to five fluorine atoms, $C_{3-6}$alkenyl, $C_{3-6}$alkynyl, $C_{3-10}$cycloalkyl$C_{0-6}$alkyl, $C_{4-12}$bridged cycloalkyl, $A(CR^4R^5)_n$ and $B(CR^4R^5)_n$;
$R^2$ is $C_{1-2}$alkyl substituted by one to five fluorine atoms;
$R^3$ is selected from the group consisting of $C_{1-6}$alkyl, $NH_2$ and $R^7CONH$;
$R^4$ and $R^5$ are independently selected from H or $C_{1-6}$alkyl;
A is an unsubstituted 5- or 6-membered heteroaryl or an unsubstituted 6-membered aryl, or a 5- or 6-membered heteroaryl or a 6-membered aryl substituted by one or more $R^6$;
$R^6$ is selected from the group consisting of halogen, $C_{1-6}$alkyl, $C_{1-6}$alkyl substituted by one more fluorine atoms, $C_{1-6}$alkoxy, $C_{1-6}$alkoxy substituted by one or more F, $NH_2SO_2$ and $C_1$alkyl$SO_2$;

B is selected from the group consisting of

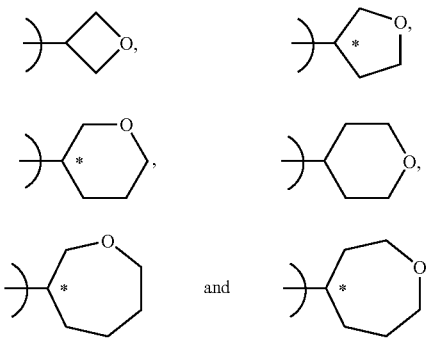

where

)

defines the point of attachment of the ring;
$R^7$ is selected from the group consisting of H, $C_{1-6}$alkyl, $C_{1-6}$alkoxy, $C_{1-6}$alkylOC$_{1-6}$alkyl, phenyl, $HO_2CC_{1-6}$alkyl, $C_{1-6}$alkylOCOC$_{1-6}$alkyl, $C_{1-6}$alkylOCO, $H_2NC_{1-6}$alkyl, $C_{1-6}$alkylOCONHC$_{1-6}$alkyl and $C_{1-6}$alkylCONHC$_{1-6}$alkyl; and n is 0 to 4.

The term halogen is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

The term 5-membered heteroaryl means a heteroaryl selected from the following:

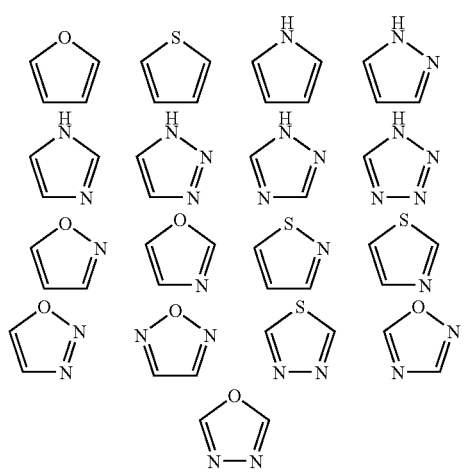

The term 6-membered heteroaryl means a heteroaryl selected from the following:

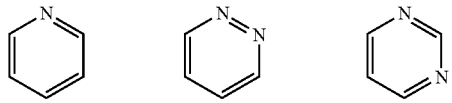

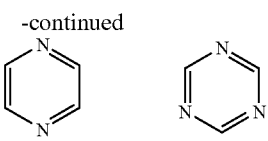

The term 6-membered aryl means:

It is to be understood that the present invention encompasses all isomers of the compounds of formula (I) and their pharmaceutically acceptable derivatives, including all geometric, tautomeric and optical forms, and mixtures thereof (e.g. racemic mixtures). In particular when the ring B lacks a plane of symmetry the compounds of formula (I) contain a chiral centre as indicated therein by the asterisk *. Furthermore, it will be appreciated by those skilled in the art that when $R^4$ and $R^5$ in formula (I) are different the corresponding compounds contain at least one chiral centre, by virtue of the asymmetric carbon atom defined thereby, and that such compounds exist in the form of a pair of optical isomers (i.e. enantiomers).

In one aspect of the invention $R^1$ is selected from the group consisting of H, $C_{1-6}$alkyl, $C_{1-2}$alkyl substituted by one to five fluorine atoms, $C_{3-6}$alkenyl, $C_{3-6}$alkynyl, $C_{3-10}$cycloalkyl$C_{0-6}$alkyl, $C_{4-12}$bridged cycloalkyl and $B(CR^4R^5)_n$;

In another aspect of the invention $R^1$ is $C_{1-6}$alkyl or $C_{1-2}$alkyl substituted by one to five fluorine atoms. In another aspect $R^1$ is $C_{2-6}$alkyl (e.g. n-butyl).

In another aspect of the invention $R^1$ is $C_{3-10}$cycloalkyl$C_{0-6}$alkyl, such as $C_{3-10}$cycloalkyl (e.g. cyclopentyl or cyclohexyl). In another aspect $R^1$ is $C_{3-10}$cycloalkylmethyl, such as $C_{3-7}$cycloalkylmethyl (e.g. cyclopentylmethyl).

In another aspect of the invention $R^1$ is $A(CR^4R^5)_n$.

In another aspect of the invention $R^2$ is $CHF_2$, $CH_2F$ or $CF_3$. In another aspect $R^2$ is $CF_3$.

In another aspect of the invention $R^3$ is $C_{1-6}$alkyl, such as $C_{1-3}$alkyl (e.g. methyl).

In another aspect of the invention $R^4$ and $R^5$ are independently selected from H or methyl. In another aspect $R^4$ and $R^5$ are both H.

In another aspect of the invention A is selected from the group consisting of

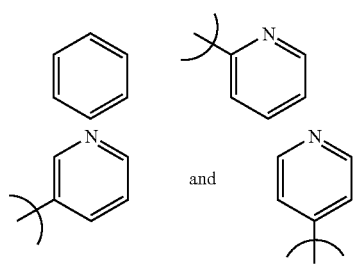

where

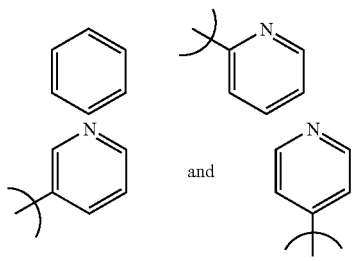

defines the point of attachment of the ring and A is unsubstituted or substituted by one or two $R^6$.

In another aspect of the invention $R^6$ is selected from the group consisting of halogen (e.g. F), $C_{1-3}$alkyl (e.g. methyl), $C_{1-3}$alkyl substituted by one to three fluorine atoms (e.g. $CF_3$), and $C_{1-3}$alkoxy (e.g. methoxy).

In another aspect of the invention $R^7$ is selected from the group consisting of $C_{1-6}$alkyl (e.g. ethyl), phenyl and aminomethyl.

In another aspect of the invention n is 1 to 4.
In another aspect of the invention n is 0 to 2 (e.g. 0).
It is to be understood that the invention covers all combinations of particular aspects of the invention as described hereinabove.

Within the invention there is provided one group of compounds of formula (I) (group A) wherein: $R^1$ is $C_{1-6}$alkyl (e.g. n-butyl); $R^2$ is $CF_3$; and $R^3$ is $C_{1-6}$alkyl, such as $C_{1-3}$alkyl (e.g. methyl).

Within the invention there is provided another group of compounds of formula (I) (group B) wherein: $R^1$ is $C_{3-10}$cycloalkyl$C_{0-6}$alkyl, such as $C_{3-10}$cycloalkyl (e.g. cyclopentyl or cyclohexyl); $R^2$ is $CF_3$; and $R^3$ is $C_{1-6}$alkyl, such as $C_{1-3}$alkyl (e.g. methyl).

Within the invention there is provided another group of compounds of formula (I) (group C) wherein: $R^1$ is $C_{3-10}$cycloalkylmethyl, such as $C_7$cycloalkylmethyl (e.g. cyclopentylmethyl); $R^2$ is $CF_3$; and $R^3$ is $C_{1-6}$alkyl, such as $C_{1-3}$alkyl (e.g. methyl).

Within the invention there is provided another group of compounds of formula (I) (group D) wherein: $R^1$ is $A(CR^4R^5)_n$; $R^2$ is $CF_3$; $R^3$ is $C_{1-6}$alkyl, such as $C_{1-3}$alkyl (e.g. methyl); $R^4$ and $R^5$ are independently selected from H or methyl; A is selected from the group consisting of and A is unsubstituted or substituted by one or two $R^6$; $R^6$ is selected from the group consisting of halogen (e.g. F), $C_{1-3}$alkyl (e.g. methyl), $C_{1-3}$alkyl substituted by one to three fluorine atoms (e.g. $CF_3$), and $C_{1-3}$alkoxy (e.g. methoxy); and n is 0 to 2 (e.g. 0).

Within group D, there is provided a further group of compounds (group D1) wherein: $R^1$ is $A(CR^4R^5)_n$; $R^2$ is $CF_3$; $R^3$ is methyl; $R^4$ and $R^5$ are both H; A is selected from the group consisting of

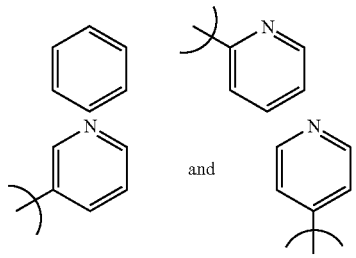

and A is unsubstituted or substituted by one or two $R^6$; $R^6$ is selected from the group consisting of fluorine, chlorine, methyl, $CF_3$ and methoxy; and n is 0 or 1.

In a preferred aspect the invention provides the following compounds:
2-(4-fluorophenoxy)-4-[4-(methylsulfonyl)phenyl]-6] (trifluoromethyl)pyrimidine;
2-(4-methoxyphenoxy)-4-[4-(methylsulfonyl)phenyl]-6-trifluoromethyl)pyrimidine;
2-butoxy-4-[4-(methylsulfonyl)phenyl]-6-(trifluoromethyl) pyrimidine;
2-[(5-chloropyridin-3-yl)oxy]-4-[4-(methylsulfony) phenyl]-6-(trifluoromethyl)pyrimidine;
2-(cyclohexyloxy)-4-[4-(methylsulfonyl)phenyl]-6-(trifluoromethyl)pyrimidine.

In a more preferred aspect the invention provides the following compound: 2-butoxy-4-[4-(methylsulfonyl) phenyl]-6-(trifluoromethyl)pyrimidine.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compound of formula (I) may be used for preparing the more pure forms used in pharmaceutical compositions. Although the purity of intermediate compounds of the present invention is less critical, it will be readily understood that the substantially pure form is preferred as for the compounds of formula (I). Preferably, whenever possible, the compounds of the present invention are available in crystalline form.

When some of the compounds of this invention are allowed to crystallise or are recrysallised from organic solvents, solvent of recrystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all the polymorphic forms of the compounds of formula (I).

Compounds of the invention are potent and selective inhibitors of COX-2. This activity is illustrated by their ability to selectively inhibit COX-2 over COX-1.

In view of their selective COX-2 inhibitory activity, the compounds of the present invention are of interest for use in human and veterinary medicine, particularly in the treatment of the pain (both chronic and acute), fever and inflammation of a variety of conditions and diseases mediated by selective inhibition of COX-2. Such conditions and diseases are well known in the art and include rheumatic fever; symptoms associated with influenza or other viral infections, such as the common cold; lower back and neck pain; headache; toothache; sprains and strains; myositis; sympathetically maintained pain; synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

The compounds of the invention are also useful for the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of the invention are also useful for the treatment of other conditions mediated by selective inhibition of COX-2.

For example, the compounds of the invention inhibit cellular and neoplastic transformation and metastatic tumour growth and hence are useful in the treatment of certain cancerous diseases, such as colonic cancer and prostate cancer. The compounds of the invention are also useful in reducing the number of adenomatous colorectal polyps and thus reduce the risk of developing colon cancer. The compounds of the invention are also useful in the treatment of cancer associated with overexpression of HER-2/neu, in particular breast cancer.

Compounds of the invention also prevent neuronal injury by inhibiting the generation of neuronal free radicals (and hence oxidative stress) and therefore are of use in the treatment of stroke; epilepsy; and epileptic seizures (including grand mal, petit mal, myoclonic epilepsy and partial seizures).

Compounds of the invention also inhibit prostanoid-induced smooth muscle contraction and hence are of use in the treatment of dysmenorrhoea and premature labour.

Compounds of the invention are also useful in the treatment of liver disease, such as inflammatory liver disease, for example chronic viral hepatitis B, chronic viral hepatitis C, alcoholic liver injury, primary biliary cirrhosis, autoimmune hepatitis, nonalcoholic steatohepatitis and liver transplant rejection.

Compounds of the invention inhibit inflammatory processes and therefore are of use in the treatment of asthma, allergic rhinitis and respiratory distress syndrome; gastrointestinal conditions such as inflammatory bowel disease, Crohn's disease, gastritis, irritable bowel syndrome and ulcerative colitis; and the inflammation in such diseases as vascular disease, migraine, periarteritis nodosa, thyroiditis, aplastic anaemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

Compounds of the invention are also useful in the treatment of ophthalmic diseases such as retinitis, retinopathies, uveitis and of acute injury to the eye tissue.

Compounds of the invention are also useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment.

Compounds of the invention are also useful in the treatment of disorders ameliorated by a gastroprokinetic agent. Disorders ameliorated by gastroprokinetic agents include ileus, for example post-operative ileus and ileus during sepsis; gastroesophageal reflux disease (GORD, or its synonym GERD); gastroparesis, such as diabetic gastroparesis; and other functional bowel disorders, such as non-ulcerative dyspepsia (NUD) and non-cardiac chest pain (NCCP).

According to a further aspect of the invention, we provide a compound of formula (I) for use in human or veterinary medicine.

According to another aspect of the invention, we provide a compound of formula (I) for use in the treatment of a condition which is mediated by COX-2.

According to a further aspect of the invention, we provide a method of treating a human or animal subject suffering from a condition which is mediated by COX-2 which comprises administering to said subject an effective amount of a compound of formula (I).

According to a further aspect of the invention, we provide a method of treating a human or animal subject suffering from an inflammatory disorder, which method comprises administering to said subject an effective amount of a compound of formula (I).

According to another aspect of the invention, we provide the use of a compound of formula (I) for the manufacture of a therapeutic agent for the treatment of a condition which is mediated by COX-2.

According to another aspect of the invention, we provide the use of a compound of formula (I) for the manufacture of a therapeutic agent for the treatment of an inflammatory disorder.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor α; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine. It is to be understood that the present invention covers the use of a compound of formula (I) in combination with one or more other therapeutic agents.

The compounds of formula (I) are conveniently administered in the form of pharmaceutical compositions. Thus, in another aspect of the invention, we provide a pharmaceutical composition comprising a compound of formula (I) adapted for use in human or veterinary medicine. Such compositions may conveniently be presented for use in conventional manner in admixture with one or more physiologically acceptable carriers or excipients.

The compounds of formula (I) may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I).

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) together with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 500 mg/kg, such as 0.05 mg/kg to 100 mg/kg, e.g. 0.1 mg/kg to 50 mg/kg, which may be conveniently administered in 1 to 4 doses. The precise dose employed will depend on the age and condition of the patient and on the route of administration. Thus, for example, a daily dose of 0.25 mg/kg to 10 mg/kg may be suitable for systemic administration.

Compounds of formula (I) may be prepared by any method known in the art for the preparation of compounds of analogous structure.

Compounds of formula (I) may be prepared by a process which comprises:
reacting an alcohol $R^1OH$ of formula (II) or a protected derivative thereof with a compound of formula (III)

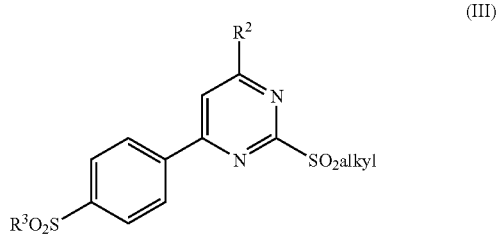

(III)

and thereafter and if necessary,
interconverting a compound of formula (I) into another compound of formula (I); and/or
deprotecting a protected derivative of compound of formula (I).

The overall synthesis of a compound of formula (I) is shown in Scheme 1 below in which, $R^1$ and $R^2$ are as defined in formula (I) above unless otherwise stated, $R^3$ is $C_{1-6}$alkyl; THF is tetrahydrofuran; MTBE is methyl t-butyl ether; and alkyl is a straight or branched chain alkyl group, for example a methyl, ethyl, n-propyl, i-propyl, n-butyl, s-butyl or t-butyl group.

Referring to Scheme 1, the preparation of compounds of formula (I) may conveniently be achieved by the treatment of compounds of formula (III) with an alcohol of formula (II) in the presence of sodium hydride. The reaction is conveniently carried out in a solvent such as THF and at between ambient temperature and reflux.

Conveniently the oxidation shown in Scheme 1 is effected using a monopersulfate compound, such as potassium peroxymonosulfate (known as Oxone™) and the reaction is carried out in a solvent, such as an aqueous alcohol, (e.g. aqueous methanol), and at between −78° C. and ambient temperature.

Alternatively, the oxidation shown in Scheme 1 may be effected using hydrogen peroxide in the presence of catalytic sodium tungstate dihydrate. The reaction may be carried out in a solvent such as acetic acid and at between ambient temperature and reflux (e.g. 50° C.).

Referring to Scheme 1, the cyclisation of diones of formula (VI) to give the corresponding pyrimidines of formula (IV) is conveniently carried out employing a thioronium salt such as a 2-methyl-2-thiopseudourea sulfate and under reflux.

It will be appreciated by those skilled in the art that certain of the procedures described in Scheme 1 for the preparation of compounds of formula (I) or intermediates thereto may not be applicable to some of the possible substituents.

It will be further appreciated by those skilled in the art that it may be necessary or desirable to carry out the transformations described in Scheme 1 in a different order from that described, or to modify one or more of the transformations, to provide the desired compound of formula (I).

Scheme 1

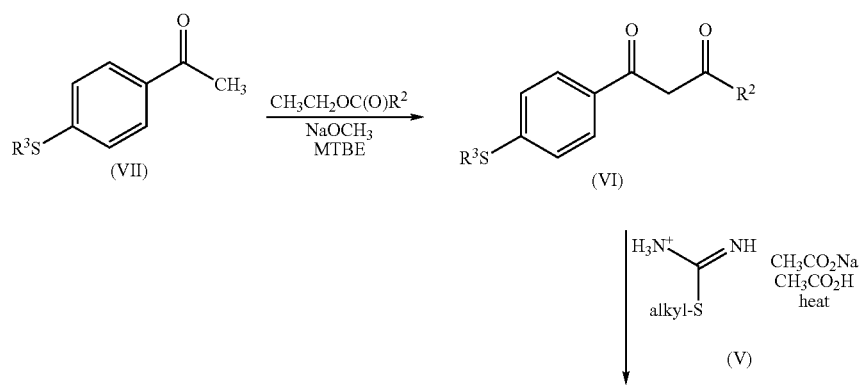

-continued

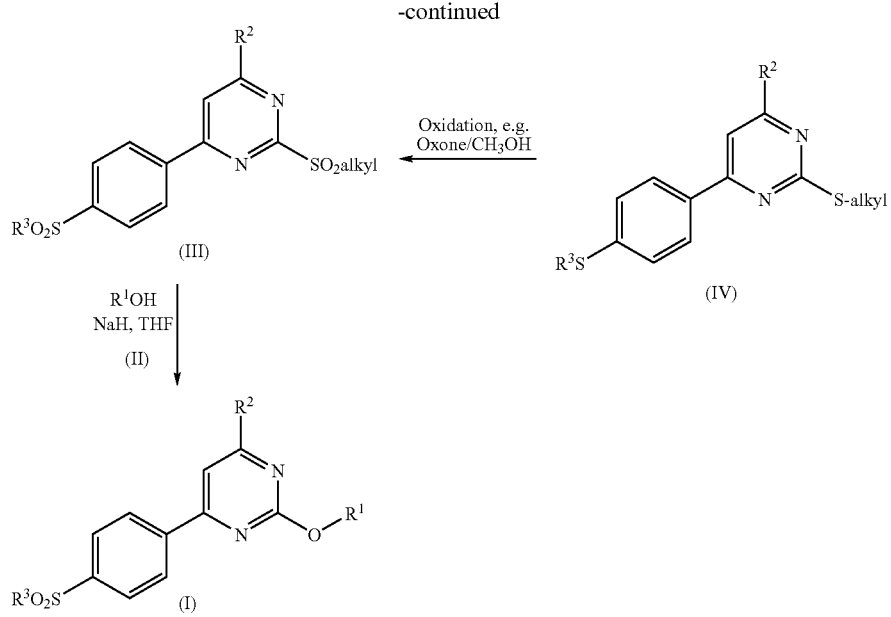

In one variation of Scheme 1, compounds of formula (III) wherein $R^3$ is $C_{1-6}$alkyl or $NH_2$ may be prepared by oxidising a compound of formula (IV)A:

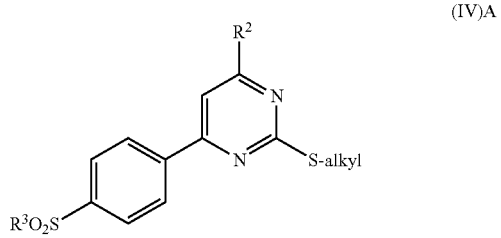

under oxidation conditions described hereinabove. Compounds of formula (IV)A may be prepared according to the general procedures of Scheme 1 by employing sulphonyl derivatives in place of the corresponding sulfide compounds of formulae (VI) and (VII).

It will be appreciated by those skilled in the art that compounds of formula (I) may be prepared by interconversion, utilising other compounds of formula (I) as precursors. Suitable interconversions, such as alkylations, are well known to those skilled in the art and are described in many standard organic chemistry texts, such as 'Advanced Organic Chemistry' by Jerry March, fourth edition (Wiley, 1992), incorporated herein by reference. For example, compounds of formula (I) wherein $R^1$ is $C_{1-6}$alkyl, $C_{1-2}$alkyl substituted by one to five fluorine atoms, $C_{3-6}$alkenyl, $C_{3-6}$alkynyl, $C_{3-10}$cycloalkyl$C_{0-6}$alkyl, $C_{4-12}$bridged cycloalkane, $A(CR^4R^5)_n$ (with the proviso that n is not zero) and $B(CR^4R^5)_n$ may be prepared by alkylating the corresponding compound of formula (I) wherein $R^1$ is H.

Acylation of compounds of formula (I) wherein $R^3$ is $NH_2$, to provide compounds of formula (I) wherein $R^3$ is $R^7CONH$, may be carried out by conventional means, for example by employing conventional acylating agents such as those described in 'Advanced Organic Chemistry', pp 417–424, incorporated herein by reference.

As will be appreciated by those skilled in the art it may be necessary or desirable at any stage in the synthesis of compounds of formula (I) to protect one or more sensitive groups in the molecule so as to prevent undesirable side reactions. The protecting groups used in the preparation of compounds of formula (I) may be used in conventional manner. See, for example, those described in 'Protective Groups in Organic Synthesis' by Theodora W Green and Peter G M Wuts, second edition, (John Wiley and Sons, 1991), incorporated herein by reference, which also describes methods for the removal of such groups.

Alcohols of formula (II) are either known compounds or may be prepared by literature methods, such as those described in 'Comprehensive Organic Transformations: a guide to functional group preparations' by Richard Larock (VCH, 1989), incorporated herein by reference.

Thioronium salts of formula (V) are either known compounds or may be prepared by literature methods, such as those described in A H Owens et al, Eur J Med Chem, 1988, 23(3), 295–300, incorporated herein by reference.

Acetophenones of formula (VII) are either known compounds or may be prepared by conventional chemistry.

Certain intermediates described above are novel compounds, and it is to be understood that all novel intermediates herein form further aspects of the present invention. Compounds of formulae (III) and (IV) are key intermediates and represent a particular aspect of the present invention.

Solvates (e.g. hydrates) of a compound of the invention may be formed during the work-up procedure of one of the aforementioned process steps.

The Intermediates and Examples that follow illustrate the invention but do not limit the invention in any way. All temperatures are in ° C. Flash column chromatography was carried out using Merck 9385 silica. Solid Phase Extraction (SPE) chromatography was carried out using Varian Mega Bond Elut (Si) cartridges (Anachem) under 15 mmHg vacuum. Thin layer chromatography (Tlc) was carried out on silica plates. In addition to those already defined, the following abbreviations are used: Me, methyl; Ac, acyl; DMSO, dimethylsulphoxide; TFA, trifluoroacetic acid; DME, dimethoxyethane; DCM, dichloromethane; NMP, N-methyl pyrrolidone; and MTBE, methyl t-butyl ether.

Intermediate 1

4,4,4-Trifluoro-1-[4-(methylthio)phenyl]butane-1,3-dione

To a solution of ethyl trifluoroacetate (7.95 ml, 1.1 eq) in MTBE (125 ml) was added dropwise 25% sodium methoxide in methanol (16 ml, 1.2 eq). 4-Methylthioacetophenone (Aldrich, 10 g, 0.06 mol) was added portionwise and the mixture stirred at ambient temperature overnight. 2N Hydrochloric acid (40 ml) was added cautiously and the organic phase separated, washed with brine and dried ($Na_2SO_4$) to give an orange solid. The orange solid was recrystallised from hot isopropanol to give the title compound as a yellow crystalline solid (11.25 g, 71%).

MH−261

Intermediate 2

2-(Methylthio)-4-[4-(methylthio)phenyl]-6-(trifluoromethyl)pyrimidine

To a mixture of 4,4,4-trifluoro-1-[4-(methylthio)phenyl] butane-1,3-dione (5 g) and 2-methyl-2-thiopseudourea sulfate (5.1 g, 0.98 eq) in acetic acid (100 ml) was added sodium acetate (3 g, 2 eq) and heated under reflux for 8 h. The mixture was concentrated in vacuo and water (100 ml) added to give a solid, which was isolated by filtration to give the title compound as a yellow solid (5.8 g, quantitative).

MH+317

Intermediate 3

2-(Methylsulfonyl)-4-[4-(methylsulfonyl)phenyl]-6-(trifluoromethyl)pyrimidine To a solution of 2-(methylthio)-4-[4-(methylthio)phenyl]-6-(trifluoromethyl)pyrimidine (5.78 g) in MeOH (500 ml) was added a solution of OXONE™ (Aldrich, 56.23 g, 5 eq) in water (200 ml). The mixture was stirred at ambient temperature overnight, concentrated in vacuo and the residue partitioned between water and ethyl acetate (2×100 ml). The combined organic phases were dried and concentrated in vacuo to an off-white solid which was triturated with hot isopropanol to give the title compound as a white solid (5.6 g, 80%).

MH+381 Tlc $SiO_2$ Ethyl acetate:cyclohexane (1:1) Rf 0.45

EXAMPLE 1

2-(4-Fluorophenoxy)-4-[4-(methylsulfonyl)phenyl]-6-(trifluoromethyl)pyrimidine.

To a stirred solution of 4-fluorophenol (37 mg, 0.33 mmole) in dry tetrahyrofuran (10 ml) was added, under an atmosphere of nitrogen, sodium hydride (60% dispersion in oil, 13 mg, 0.33 mmole) and the resulting mixture stirred at 20 for 30 min. To the stirred reaction mixture was added 2-(methylsulfonyl)-4[4-(methylsulfonyl)phenyl]-6-trifluoromethyl)pyrimidine (114 mg, 0.33 mmole) in a single portion, and stirring was continued for 2 h. The solvent was evaporated, and the residue partitioned between dichloromethane and 2N sodium hydroxide. The dried organic phase was evaporated to dryness. The residue was purified on a silica gel SPE cartridge eluting with chloroform to afford the title compound as a colourless solid (99 mg, 80%).

MH+413.

EXAMPLES 2 to 10

Examples 2 to 10, as shown in Table 1 that follows, were prepared in the manner described for Example 1.

TABLE 1

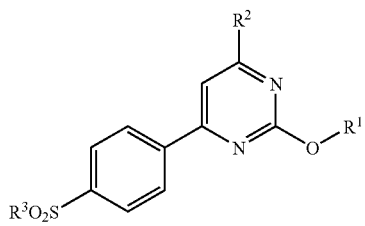

(I)

| Ex | $R^1$ | $R^2$ | $R^3$ | MS | |
|----|-------|-------|-------|-----|-----|
| 2 | 3,4-difluorophenyl | $CF_3$ | $CH_3$ | MH+ | 431 |
| 3 | 4-methoxyphenyl | $CF_3$ | $CH_3$ | MH+ | 425 |
| 4 | 4-fluorobenzyl | $CF_3$ | $CH_3$ | MH+ | 427 |
| 5 | 4-bromophenyl | $CF_3$ | $CH_3$ | MH+ | 474 |
| 6 | 4-methylphenyl | $CF_3$ | $CH_3$ | MH+ | 409 |
| 7 | 5-chloropyridin-3-yl | $CF_3$ | $CH_3$ | MH+ | 431 |
| 8 | cyclohexyl | $CF_3$ | $CH_3$ | MH+ | 401 |
| 9 | cyclopentylmethyl | $CF_3$ | $CH_3$ | MH+ | 401 |
| 10 | n-butyl | $CF_3$ | $CH_3$ | MH+ | 375 |

EXAMPLE 11

2-Butoxy-4-[4-(methylsulfonyl)phenyl]-6-(trifluoromethyl)pyrimidine

Sodium methoxide (6.6 kg of a 30% w/w solution in methanol) was added over at least 30 min to a solution of 4-(methylthio)acetophenone (5.0 kg) and methyl trifluoroacetate (4.25 kg) in tert-butylmethylether (40 L) at 40±3° C. The solution was heated at 40±3° C. for at least 3 h. Acetic acid (55 L) was added, followed by S-methyl 2-thiopseudourea sulfate (5.45 kg) and the mixture concentrated to ca. 45 L. The mixture was heated at about 110° C. for at least a further 8 h (overnight) then acetic acid (20 L) was added before cooling to 50±3° C. A solution of sodium tungstate dihydrate (0.2 kg) in water (2.5 L) was added, followed by hydrogen peroxide (20.7 kg of 30% w/v solution), which was added over at least 3 h, maintaining the temp at ca. 50°. The mixture is heated at ca. 50° C. for at least 12 h before cooling to 20±3° C. A solution of sodium sulphite (3.45 kg) in water (28 L) was then added over at least 30 min whilst maintaining the temperature at 20±3°. The mixture was aged at 20±3° C. for ca. 1 h and 2-(methylsulfonyl)-4-[4-(methylsulfonyl)phenyl]-6-(trifluoromethyl)pyrimidine collected by filtration, washed with water (3×15 L) and dried at up to 60° in vacuo.

Yield, 9.96 kg, 90% of theory.

A suspension of 2-(methylsulfonyl)-4-[4-(methylsulfonyl)phenyl]-6-(trifluoromethyl)pyrimidine (525 g) in n-butanol (5.25 L) was treated with potassium carbonate (210 g) at 20±5° C. The mixture was heated to 50±5° C. overnight until the reaction was complete by HPLC. Acetic acid (1.57 L) was added dropwise, to control any gas evolution, keeping the temperature at 50±5° C. Water (3.67 L) was then added over 30 min keeping the temperature at 50±5° C. to allow full crystallisation to occur. The slurry was then cooled to 20–25° C. and aged for at least 1 hour. The resulting product was then filtered under vacuum and washed with a mixture of n-butanol (787 mL), acetic acid (236 mL), and water (551 mL) followed by water (2×1.57 L). The product was then dried at up to ca50° C. under vacuum to yield the title compound. Yield, 457 g, 88.4% of theory. The title compound was found to be identical to that of Example 10.

$^1$H NMR (CDCl$_3$) δ: 8.33(2H, d, para-di-substituted CH); 8.11(2H, d, para-di-substituted CH); 7.70(1H, s, aromatic CH); 4.54(2H, t, butyl CH$_2$); 3.12(3H, s, sulphone CH$_3$); 1.88(2H, m, butyl CH$_2$); 1.55(2H, m, butyl CH$_2$); 1.01(3H, t, butyl CH$_3$).

Biological Data

Cell Based Assay

Inhibitory activity against human COX-1 and COX-2 was assessed in COS cells which had been stably transfected with cDNA for human COX-1 and human COX-2. 24 Hours prior to experiment, COS cells were transferred from the 175 cm$^2$ flasks in which they were grown, onto 24-well cell culture plates using the following procedure. The incubation medium (Dulbecco's modified eagles medium (DMEM) supplemented with heat-inactivated foetal calf serum (10% v/v), penicillin (100 IU/ml), streptomycin (100 μg/ml) and geneticin (600 μg/ml)) was removed from a flask of confluent cells (1 flask at confluency contains approximately 1×10$^7$ cells). 5 ml of phosphate buffered saline (PBS) was added to the flask to wash the cells. Having discarded the PBS, cells were then incubated with 5 ml trypsin for 5 minutes in an incubator (37°). The flask was then removed from the incubator and 5 ml of fresh incubation medium was added. The contents of the flask was transferred to a 250 ml sterile container and the volume of incubation medium subsequently made up to 100ml. 1 ml cell suspension was pipetted into each well of 4×24-well cell culture plates. The plates were then placed in an incubator (37° C., 95% air/5% CO$_2$) overnight. If more than 1 flask of cells were required, the cells from the individual flasks were combined before being dispensed into the 24-well plates.

Following the overnight incubation, the incubation medium was completely removed from the 24-well cell culture plates and replaced with 250 μl fresh DMEM (37° C.). The test compounds were made up to 250× the required test concentration in DMSO and were added to the wells in a volume of 1 μl. Plates were then mixed gently by swirling and then placed in an incubator for 1 hour (37° C., 95% air/5% CO$_2$). Following the incubation period, 10 μl of arachidonic acid (750 μM) was added to each well to give a final arachidonic acid concentration of 30 μM. Plates were then incubated for a further 10 minutes, after which the incubation medium was removed from each well of the plates and stored at −20° C., prior to determination of prostaglandin E$_2$ (PGE2) levels using enzyme immunoassay. The inhibitory potency of the test compound was expressed as an IC$_{50}$ value, which is defined as the concentration of the compound required to inhibit the PGE2 release from the cells by 50%. The selectivity ratio of inhibition of COX-1 versus COX-2 was calculated by comparing respective IC$_{50}$ values.

The following IC$_{50}$ values for inhibition of COX-2 and COX-1 were obtained from the cell based assay for compounds of the invention:

| Example No. | COX-2: IC$_{50}$ (nM) | COX-1: IC$_{50}$ (nM) |
| --- | --- | --- |
| 1 | <1 | 81,300 |
| 2 | 23 | 9,675 |
| 3 | 4 | 2,923 |
| 5 | 6 | 61,380 |

Microsomal Assay

Inhibitory activity against microsomal h-COX2 was assessed against a microsomal preparation from baculovirus infected SF9 cells. An aliquot of microsomal preparation was thawed slowly on ice and a 1/40,000 dilution prepared from it into the assay buffer (sterile water, degassed with argon containing 100 mM HEPES (pH 7.4), 10 mM EDTA (pH7.4), 1 mM phenol, 1 mM reduced glutathione, 20 mg/ml gelatin and 0.001 mM Hematin). Once diluted the enzyme solution was then sonicated for 5 seconds (Branson sonicator, setting 4, 1 cm tip) to ensure a homogeneous suspension. 155 μl enzyme solution was then added to each well of a 96-well microtitre plate containing either 5 μl test compound (40× required test concentration) or 5 μl DMSO for controls. Plates were then mixed and incubated at room temperature for 1 hour. Following the incubation period, 40 μl of 0.5 μM arachidonic acid was added to each well to give a final concentration of 0.1 μM. Plates were then mixed and incubated for exactly 10 minutes (room temperature) prior to addition of 25 μM HCl (hydrochloric acid) to each well to stop the reaction. 25 μl of 1 M NaOH (sodium hydroxide) was then added to each well to neutralise the solution prior to determination of PGE$_2$ levels by enzyme immunoassay (EIA).

The following IC$_{50}$ values for inhibition of COX-2 and COX-1 were obtained from the microsomal assay for compounds of the invention:

| Example No. | COX-2: IC$_{50}$ (nM) | COX-1: IC$_{50}$ (nM) |
| --- | --- | --- |
| 6 | <10 | 3,752 |
| 7 | <10 | 79,889 |
| 8 | <10 | 1,860 |
| 9 | 22 | 69,000 |
| 10 | 22 | >30000 |

What is claimed is:

1. A compound of formula (I)

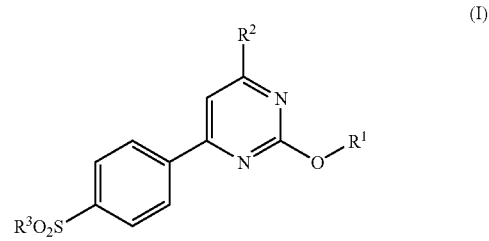

in which:

R$^1$ is selected from the group consisting of H, C$_{1-6}$alkyl, C$_{1-2}$alkyl substituted by one to five fluorine atoms, C$_{3-6}$alkenyl, C$_{3-6}$alkynyl, C$_{3-10}$cycloalkylC$_{0-6}$alkyl, C$_{4-12}$bridged cycloalkyl, A(CR$^4$R$^5$)$_n$ and B(CR$^4$R$^5$)$_n$;

R$^2$ is C$_{1-2}$alkyl substituted by one to five fluorine atoms;

R$^3$ is selected from the group consisting of C$_{1-6}$alkyl, NH$_2$ and R$^7$CONH;

R$^4$ and R$^5$ are independently selected from H or C$_{1-6}$alkyl;

A is an unsubstituted 5- or 6-membered heteroaryl or an unsubstituted 6-membered aryl, or a 5- or 6-membered heteroaryl or a 6-membered aryl substituted by one or more R$^6$;

R$^6$ is selected from the group consisting of halogen, C$_{1-6}$alkyl, C$_{1-6}$alkyl substituted by one more fluorine atoms, C$_{1-6}$alkoxy, C$_{1-6}$alkoxy substituted by one or more F, NH$_2$SO$_2$ and C$_{1-6}$alkylSO$_2$;

B is selected from the group consisting of

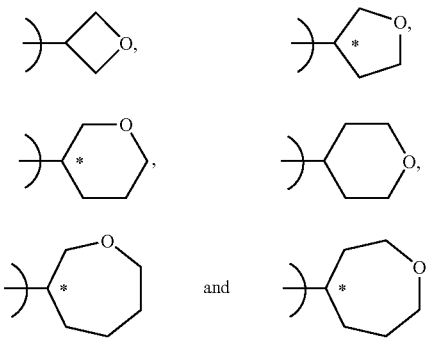

where

defines the point of attachment of the ring;

$R^7$ is selected from the group consisting of H, $C_{1-6}$alkyl, $C_{1-6}$alkoxy, $C_{1-6}$alkylO$C_{1-6}$alkyl, phenyl, HO$_2$CC$_{1-6}$alkyl, $C_{1-6}$alkylOCO$C_{1-6}$alkyl, $C_{1-6}$alkylOCO, H$_2$NC$_{1-6}$alkyl, $C_{1-6}$alkylOCONHC$_{1-6}$alkyl and $C_{1-6}$alkylCONHC$_{1-6}$alkyl; and n is 0 to 4.

2. The compound as claimed in claim 1 wherein $R^1$ is selected from the group consisting of $C_{1-6}$alkyl, $C_{1-2}$alkyl substituted by one to five fluorine atoms, $C_{3-10}$cycloalkyl $C_{0-6}$alkyl and $A(CR^4R^5)_n$.

3. The compound as claimed in claim 1 wherein $R^2$ is CHF$_2$, CH$_2$F or CF$_3$.

4. The compound as claimed in claim 1 wherein $R^3$ is $C_{1-6}$alkyl.

5. The compound as claimed in claim 1 wherein $R^4$ and $R^5$ are independently selected from H or methyl.

6. The compound as claimed in claim 1 wherein A is selected from the group consisting of

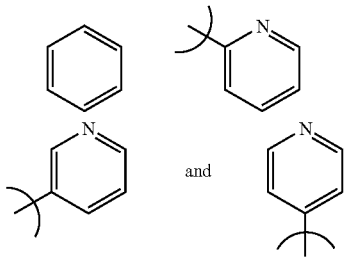

where

defines the point of attachment of the ring
and A is unsubstituted or substituted by one or two $R^6$.

7. The compound as claimed in claim 1 wherein $R^6$ is selected from the group consisting of halogen, $C_{1-3}$alkyl, $C_{1-3}$alkyl substituted by one to three fluorine atoms, and $C_{1-3}$alkoxy.

8. The compound as claimed in claim 1 wherein $R^7$ is selected from the group consisting of $C_{1-6}$alkyl, phenyl and aminomethyl.

9. The compound as claimed in claim 1 wherein n is 0 to 2.

10. The compound as claimed in claim 1 wherein $R^1$ is $C_{1-6}$alkyl; $R^2$ is CF$_3$; and $R^3$ is $C_{1-6}$alkyl.

11. The compound as claimed in claim 1 wherein $R^1$ is $C_{3-10}$cycloalkyl$C_{0-6}$alkyl; $R^2$ is CF$_3$; and $R^3$ is $C_{1-6}$alkyl.

12. The compound as claimed in claim 1 wherein $R^1$ is $C_{3-10}$cycloalkylmethyl; $R^2$ is CF$_3$; and $R^3$ is $C_{1-6}$alkyl.

13. The compound as claimed in claim 1 wherein $R^1$ is $A(CR^4R^5)_n$; $R^2$ is CF$_3$; $R^3$ is methyl; $R^4$ and $R^5$ are both H; A is selected from the group consisting of

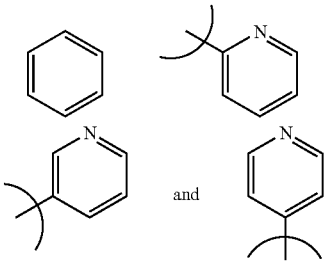

and A is unsubstituted or substituted by one or two $R^6$; $R^6$ is selected from the group consisting of fluorine, chlorine, methyl, CF$_3$ and methoxy; and n is 0 or 1.

14. The compound according to claim 1, wherein $R^1$ is $C_{1-6}$alkyl; $R^2$ is CF$_3$; and $R^3$ is $C_{1-3}$alkyl.

15. The compound as claimed in claim 1 wherein $R^1$ is $C_{3-10}$cycloalkyl; $R^2$ is CF$_3$; and $R^3$ is $C_{1-3}$alkyl.

16. The compound as claimed in claim 1 wherein $R^1$ is $C_{3-7}$cycloalkylmethyl; $R^2$ is CF$_3$; and $R^3$ is $C_{1-3}$alkyl.

17. 2-Butoxy-4-[4-(methylsulfonyl)phenyl]-6-(trifluoromethyl)pyrimidine.

18. A compound selected from 2-(4-fluorophenoxy)-4-[4-(methylsulfonyl)phenyl]-6] (trifluoromethyl)pyrimidine;

2-(4-methoxyphenoxy)-4-[4-(methylsulfonyl)phenyl]-6-trifluoromethyl)pyrimidine;

2-butoxy-4-[4-(methylsulfonyl)phenyl]-6-(trifluoromethyl)pyrimidine;

2-[(5-chloropyridin-3-yl)oxy]-4-[4-(methylsulfony) phenyl]-6-(trifluoromethyl)pyrimidine; and 2-(cyclohexyloxy)-4-[4-(methylsulfonyl)phenyl]-6-(trifluoromethyl)pyrimidine.

19. A process for the preparation of a compound as defined in claim 1, which comprises:

(A), reacting an alcohol $R^1$OH of formula (II) or a protected derivative thereof with a compound of formula (III)

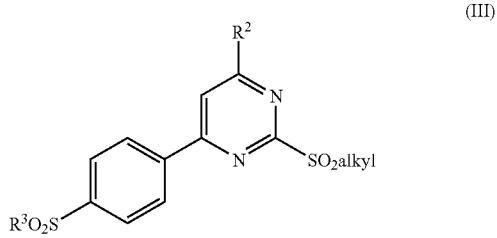

and thereafter and if necessary, (B), interconverting a compound of formula (I) into another compound of formula (I); and/or (C), deprotecting a protected derivative of compound of formula (I).

20. A pharmaceutical composition comprising a compound as defined in claim 1 in admixture with one or more physiologically acceptable carriers or excipients.

21. A method of treating a subject suffering from arthritis which comprises administering to said subject an effective amount of a compound as claimed in claim 1.

22. The method according to claim 21, wherein said subject is a human.

23. The method according to claim 21 wherein said arthritis is rheumatoid arthritis.

24. The method according to claim 21 wherein said compound is 2-Butoxy-4-[4-(methylsulfonyl)phenyl]-6-(trifluoromethyl)pyrimidine.

25. A method of treating a subject suffering from osteoarthritis which comprises administering to said subject an effective amount of a compound as claimed in claim 1.

26. A method of treating a subject suffering from acute or chronic pain which comprises administering to said subject an effective amount of a compound as claimed in claim 1.

27. The method according to claim 26, wherein said subject is a human.

28. The method according to claim 26 wherein said acute or chronic pain is lower back or neck pain.

29. The method according to claim 26 wherein said acute or chronic pain is neuropathic pain.

30. The method according to claim 26 wherein said acute or chronic pain is non-specific lower back pain.

31. The method according to claim 26 wherein said acute or chronic pain is post-herpetic neuralgia.

32. A method of treating a subject suffering from dysmenorrhoea which comprises administering to said subject an effective amount of a compound as claimed in claim 1.

33. A method of treating a human suffering from rheumatoid arthritis which comprises administering to said human an effective amount of 2-Butoxy-4-[4-(methylsulfonyl)phenyl]-6-(trifluoromethyl)pyrimidine.

34. A method of treating a human suffering from osteoarthritis which comprises administering to said human an effective amount of 2-Butoxy-4-[4-(methylsulfonyl)phenyl]-6-(trifluoromethyl)pyrimidine.

35. A method of treating a human suffering from non-specific lower back pain which comprises administering to said human an effective amount of 2-Butoxy-4-[4-(methylsulfonyl)phenyl]-6-(trifluoromethyl)pyrimidine.

36. A method of treating a human suffering from post-herpetic neuralgia which comprises administering to said human an effective amount of 2-Butoxy-4-[4-(methylsulfonyl)phenyl]-6-(trifluoromethyl)pyrimidine.

37. A method of treating a human suffering from dysmenorrhoea which comprises administering to said human an effective amount of 2-Butoxy-4-[4-(methylsulfonyl)phenyl]-6-(trifluorormethyl)pyrimidine.

* * * * *